United States Patent [19]

D'Amico

[11] 4,229,578

[45] Oct. 21, 1980

[54] PROCESS FOR PREPARING THIOESTERS

[75] Inventor: John J. D'Amico, Olivette, Mo.

[73] Assignee: Monsanto Company, St. Louis, Mo.

[21] Appl. No.: 946,983

[22] Filed: Sep. 29, 1978

[51] Int. Cl.$^2$ .................. C07D 277/68; C07C 153/07
[52] U.S. Cl. ............................... 548/165; 260/455 R; 71/100; 71/72
[58] Field of Search ...................... 260/304 B, 455 R; 548/165

[56] References Cited

PUBLICATIONS

Bulmer et al., J. Chem. Soc. (1945), pp. 677–680.
Cram et al., "Organic Chem.", 2nd Ed., pp. 339 and 360, McGraw Hill (1964).

Primary Examiner—Donald G. Daus
Assistant Examiner—D. B. Springer
Attorney, Agent, or Firm—Richard H. Shear; Donald W. Peterson

[57] ABSTRACT

Thioesters are prepared by the reaction of acid halides and xanthates.

7 Claims, No Drawings

PROCESS FOR PREPARING THIOESTERS

This invention relates to a novel process for preparing thioesters. More particularly, the invention relates to the preparation of thioesters by reaction of an acid halide with a xanthate.

Thioesters are known to be useful agricultural chemicals. U.S. Pat. No. 3,282,977 discloses the use of several thioesters as herbicides for preventing the growth of undesirable weeds. U.S. Pat. No. 3,445,221 discloses the use of other thioesters for desiccating cotton. Copending application Ser. No. 835,129 discloses the use of still other thioesters in the regulation of desirable crop plants. In each instance, the thioesters were prepared by reaction of an acid chloride with a mercaptan.

As will be appreciated by those skilled in the art, mercaptans are highly toxic, odoriferous compounds that are easily oxidizable to the corresponding disulfide. Replacement of the mercaptan with a non-toxic, odor-free reactant would certainly be advantageous.

An object of the present invention, then, is to replace the mercaptan used in the process for preparing thioesters by a relatively non-toxic, odor-free reactant.

A second object of the invention is to provide a process for preparing thioesters that is fast, efficient, economical and uncomplicated by side reactions.

These and other objects of the invention are accomplished by preparing a thioester from an acid halide and a xanthate. For purposes of clarity, the following chemical equation is presented to illustrate the simplicity of the novel process:

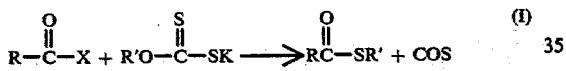

The preparation of thioesters in accordance with the above procedure is quite unexpected in view of articles such as those published by Bulmer et al, *Journal Chemical Society*, (London), page 677 (1945) wherein it is disclosed that p-nitrobenzoyl chloride and p-chlorobenzoyl chloride react with potassium ethyl xanthate to form O-ethyl S-p-nitrobenzoyl xanthate and O-ethyl S-p-chlorobenzoyl xanthate, respectively. In addition, Bulmer et al reported that reaction of acetyl chloride with potassium ethyl xanthate formed O-ethyl S-acetyl xanthate which readily decomposed to ethyl acetate and carbon disulphide. Similarly, M. M. Richter, Berichte, Vol. 49 (1916) page 1026, discloses the decomposition of O-ethyl S-acetyl xanthate to ethyl acetate and carbon disulphide.

In accordance with the present invention, it has been found that the reaction of an acid halide with a xanthate proceeds as follows:

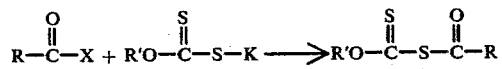

The mixed anhydride formed will either be stable or decompose by giving up carbonyl sulfide or carbon disulfide. It is postulated that the stability of the mixed anhydride is dependent upon the electrophilic properties of the R moiety. When R is weakly electrophilic, such as alkyl and phenyl, the mixed anhydride has a tendency to decompose to the corresponding ester and carbon disulfide. When R is a mono-substituted phenyl, the mixed anhydride is stable. Unexpectedly, when R is more electrophilic than alkyl, phenyl or mono-substituted phenyl, the mixed anhydride decomposes to the thioester and carbonyl sulfide. Accordingly, it has been found that the reaction proceeds in accordance with equation (I) above when R represents a radical selected from the groups consisting of aryl, aryloxy, aryloxyalkylene, each of which has been substituted on the phenyl ring with at least two substituents independently selected from the group consisting of halogen, cyano, nitro, perfluoroalkyl, alkoxy, alkylcarbonyl, alkoxyalkyl, alkylthio, alkythioalkyl and the like. R may also represent an amino-substituted alkylene wherein the nitrogen atom of the amino group is part of a heterocyclic ring. In the above equations, R' represents a radical selected from the group consisting of alkyl, alkenyl substituted with one or more chlorine atoms, benzyl and benzyl wherein the phenyl radical of said benzyl may optionally be substituted with one or more moieties independently selected from the group consisting of alkyl having up to five carbon atoms, inclusive, halogen, nitro, $CF_3$, cyano and the like. X is halogen, expecially chloro.

The above procedure is especially effective in preparing thioesters in which R' is methyl, ethyl or benzyl and R is phenyl substituted by at least two radicals independently selected from the group consisting of halogen, alkoxy, cyano, nitro and $CF_3$; phenoxy substituted by at least two radicals independently selected from the group consisting of halogen, alkoxy, cyano, nitro and $CF_3$; phenoxymethyl wherein said phenyl ring is substituted by at least two radicals independently selected from the group consisting of halogen, alkoxy, cyano, nitro and $CF_3$; and 2-oxo-3-benzothiazolinylmethyl.

Typically, inert solvents are utilized to facilitate the reaction between the acid halide and the xanthate. Examples of such solvents are acetone, benzene, chloroform, methylene chloride, toluene and tetrahydrofuran.

In order to further illustrate the process of the invention, the following examples are presented and are not intended as a limitation with respect to the scope thereof.

EXAMPLE 1

To a stirred slurry containing 0.12 moles of potassium benzyl dithiocarbonate dihydrate in 200 ml. of acetone, 0.1 moles of 2-oxo-3-benzothiazolineacetyl chloride was added in one portion. An exothermic reaction set in causing a temperature rise. After the rise in temperature subsided, the reaction mixture was stirred at 25°-30° C. for 18 hours. After 800 grams of ice water was added, stirring was continued at 0°-10° C. for 2 hours. The solid was collected by filtration, washed with water until neutral to litmus and air-dried at 25°-30° C. Data is summarized in Table I, below.

EXAMPLE 2

The procedure of Example 1 is repeated utilizing potassium methyl dithiocarbonate dihydrate in lieu of potassium benzyl dithiocarbonate dihydrate. Data is summarized in Table I, below.

EXAMPLE 3

The procedure of Example 1 is repeated utilizing 2,4-dichlorophenoxyacetyl chloride in lieu of 2-oxo-3-benzothiazolineacetyl chloride. Data is summarized in Table I, below.

EXAMPLE 4

To a stirred slurry containing 0.12 moles of potassium ethyl dithiocarbonate dihydrate in 200 ml. of acetone, 0.1 moles of 2-methoxy-3,6-dichlorobenzoyl chloride is added in one portion. An exothermic reaction set in causing a temperature rise. The reaction mixture was then stirred at 25°–30° C. for 18 hours. After 500 ml. of water and 600 ml. of ethyl ether were added, stirring was continued for 15 minutes. The separated ether layer was washed with water until the washings were neutral to litmus and dried over sodium sulfate. The ethyl ether is removed in vacuo at a maximum temperature of 80°–90° C. at 1–2 mm. Data is summarized in Table I, below.

EXAMPLE 5

The procedure of Example 4 is repeated utilizing potassium benzyl dithiocarbonate dihydrate in lieu of potassium ethyl dithiocarbonate dihydrate. Upon standing at room temperature, the product solidified. Data is summarized in Table I, below.

EXAMPLE 6

The procedure of Example 4 is repeated utilizing potassium methyl dithiocarbonate dihydrate in lieu of potassium ethyl dithiocarbonate dihydrate. Upon standing at room temperature, the product solidified. Data is summarized in Table I, below.

TABLE I $$\underset{O}{RC}-Cl + \underset{S}{R'OCSK} \longrightarrow \underset{O}{RCSR'}$$

| Compound of Ex. No. | R | R' | M.P. °C. or (bp °C./mm) | % Yield | | % C | % H | % Cl | % N | % S |
|---|---|---|---|---|---|---|---|---|---|---|
| 1 | benzothiazolinone-CH$_2$– | –CH$_2$C$_6$H$_5$ | 113–4$^a$ | 79 | Calc'd: | 60.93 | 4.15 | — | 4.44 | 20.33 |
| | | | | | Found: | 60.99 | 4.21 | — | 4.42 | 20.40 |
| 2 | benzothiazolinone-CH$_2$– | –CH$_3$ | 146–7$^b$ | 50 | Calc'd: | 50.19 | 3.79 | — | 5.85 | 26.80 |
| | | | | | Found: | 50.26 | 3.83 | — | 5.85 | 26.87 |
| 3 | 2,4-dichlorophenoxymethyl | –CH$_2$C$_6$H$_5$ | 75–6$^c$ | 83 | Calc'd: | 55.06 | 3.70 | 21.67 | — | 9.80 |
| | | | | | Found: | 55.05 | 3.71 | 21.63 | — | 9.82 |
| 4 | 2,3-dichloro-6-methoxyphenyl | –C$_2$H$_5$ | (138–9/0.2) (N$_D^{25}$ = 1.5690) | 91 | Calc'd: | 45.30 | 3.80 | 26.74 | — | 12.09 |
| | | | | | Found: | 45.08 | 3.88 | 26.58 | — | 12.20 |
| 5 | 2,3-dichloro-6-methoxyphenyl | –CH$_2$C$_6$H$_5$ | 38–9 | 95 | Calc'd: | 55.06 | 3.70 | 21.67 | — | 9.80 |
| | | | | | Found: | 54.89 | 3.57 | 21.31 | — | 10.16 |
| 6 | 2,3-dichloro-6-methoxyphenyl | –CH$_3$ | 43–4 | 76 | Calc'd: | 43.04 | 3.21 | 28.23 | — | 12.77 |
| | | | | | Found: | 42.83 | 3.21 | 28.16 | — | 12.93 |

$^a$Recrystallization from isopropyl alcohol.
$^b$Recrystallization from methyl alcohol.
$^c$Recrystallization from heptane.

As can be appreciated from the above examples, the process is preferably conducted at atmospheric pressure, although sub-atmospheric and super-atmospheric pressures may be employed. The reaction proceeds at room temperature and generally rises from 22° C. to about 40° C. due to the exothermic nature of the reaction.

Although the reaction proceeds when a stoichiometric equivalent of acid halide and xanthate is utilized, a slight excess of the xanthate is preferred.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for the preparation of thioesters having the formula

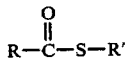

wherein R represents 2-oxo-3-benzothiazolinylmethyl; phenoxymethyl wherein said phenyl ring is substituted by two chloro radicals; or phenyl substituted by three radicals independently selected from the group consisting of chloro and methoxy; R' represents methyl, ethyl or benzyl as the principal product which consists essentially of reacting in an inert solvent an acid chloride having the formula

with a xanthate having the formula

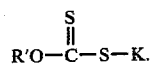

2. A process according to claim 1 wherein R is 2-oxo-3-benzothiazolinylmethyl.

3. A process according to claim 1 wherein R is 2,4-dichlorophenoxymethyl.

4. A process according to claim 1 wherein R is 2,5-dichloro-6-methoxyphenyl.

5. A process according to claim 2 wherein R' is methyl, ethyl or benzyl.

6. A process according to claim 3 wherein R' is methyl, ethyl or benzyl.

7. A process according to claim 4 wherein R' is methyl, ethyl or benzyl.